United States Patent [19]

Zaugg

[11] 4,305,938
[45] Dec. 15, 1981

[54] 2,8-DISUBSTITUTED-10-HYDROXY-5,5-DIMETHYL-TETRAHYDRO-AND HEXAHYDRO-5H-[1]-BENZOPYRANO[4,3-C]PYRIDINES, COMPOSITIONS AND USE

[75] Inventor: Harold E. Zaugg, Lake Forest, Ill.

[73] Assignee: Abbott Laboratories, North Chicago, Ill.

[21] Appl. No.: 157,740

[22] Filed: Jun. 9, 1980

[51] Int. Cl.³ ............... A61K 31/54; A61K 31/44; C07D 491/052
[52] U.S. Cl. ............... 424/246; 424/248.51; 424/248.54; 424/250; 424/256; 424/263; 424/267; 544/58.6; 544/126; 544/361; 546/89
[58] Field of Search ............ 544/126, 361, 58.6; 546/89; 424/248.51, 248.54, 246, 250, 256, 267, 263

[56] References Cited

U.S. PATENT DOCUMENTS

| Re. 29,196 | 4/1977 | Winn | 424/256 |
|---|---|---|---|
| 3,429,889 | 2/1969 | Shulgin | 546/89 |
| 3,576,798 | 4/1971 | Pars et al. | 546/89 |
| 3,991,194 | 11/1976 | Harris et al. | 424/246 |
| 4,111,942 | 9/1978 | Lee et al. | 546/89 |

Primary Examiner—Henry R. Jiles
Assistant Examiner—R. W. Ramsuer
Attorney, Agent, or Firm—Robert L. Niblack

[57] ABSTRACT

The present invention provides 2,8-disubstituted-10-hydroxy-5,5-dimethyl-tetrahydro-and hexahydro-5H-[1]-benzopyrano[4,3-c]pyridines represented by Formulae I–III:

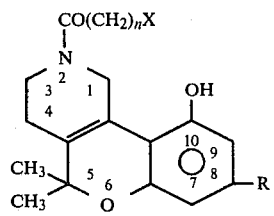

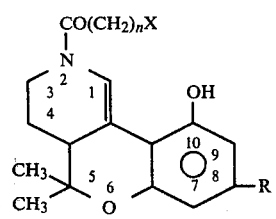

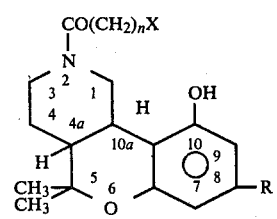

wherein: R is selected from the group consisting of $C_4$–$C_{20}$ straight or branched chain alkyl, $C_8$14 $C_{20}$ straight or branched chain arylalkyl; n is an integer from 1–4 inclusive; and X is OH; $NR_1R_2$, $R_1$ and $R_2$ being the same or different members of the group consisting of hydrogen and loweralkyl, and

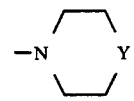

wherein Y is $CH_2$, S, O or $NR_1$; and the pharmaceutically acceptable salts thereof. The compounds are useful as antihypertensive agents.

34 Claims, No Drawings

2,8-DISUBSTITUTED-10-HYDROXY-5,5-DIMETHYL-TETRAHYDRO-AND HEXAHYDRO-5H-[1]-BENZOPYRANO[4,3-C]PYRIDINES, COMPOSITIONS AND USE

BACKGROUND OF THE INVENTION

Because the etiology of hypertension is largely unknown, the search for antihypertensive agents has been largely empirical. There currently are a number of commercially available agents, with widely varying mechanisms of action, employed in the management of hypertension. However, the search for new and improved agents continues because of the side effects of all known agents.

One approach in the search for improved hypertensive agents has been directed to the chemical modification of tetrahydrocannabinol (THC) in an effort to separate the anti-hypertensive properties of THC from the psychotropic and other pharmacological actions of THC. During the past decade, numerous derivatives were investigated, and while compounds having profound physiological effects have been discovered, to date attempts to provide an antihypertensive agent substantially devoid of psychotropic activity have been largely unsuccessful.

The present invention provides benzopyranopyridines which are useful as antihypertensive agents and which exhibit a low degree of psychotropic activity, unlike the benzopyranopyridines of U.S. Pat. Nos. 3,429,889; 3,576,798; 3,991,194; and Re. 29,196.

SUMMARY

The present invention provides 2,8-disubstituted-10-hydroxy-5,5-dimethyl-tetrahydro-and hexahydro-5H-[1]-benzopyrano[4,3-c]pyridines represented by Formulae I–III:

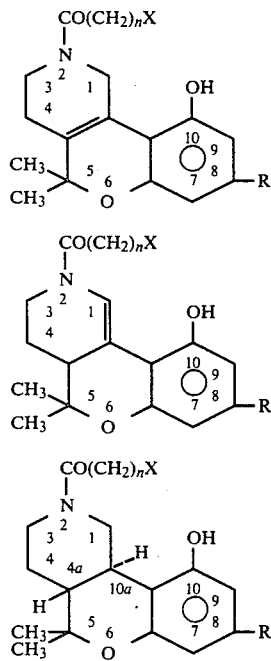

wherein: R is selected from the group consisting of $C_4$–$C_{20}$ straight or branched chain alkyl, $C_8$–$C_{20}$ straight or branched chain arylalkyl; n is an integer from 1–4 inclusive; and X is OH, $NR_1R_2$, $R_1$ and $R_2$ being the same or different members of the group consisting of hydrogen and loweralkyl, and

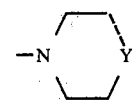

wherein Y is $CH_2$, S, O or $NR_1$; and the pharmaceutically acceptable salts thereof.

The term "loweralkyl", as used herein, refers to straight or branched chain alkyl radicals having from 1 to 6 carbon atoms, inclusive, and includes, but is not limited to methyl, ethyl, n-propyl, iso-propyl, n-butyl, iso-butyl, tert-butyl, n-pentyl, 2,2-dimethylpentyl, n-hexyl, 3-methylpentyl, and the like.

The term "$C_4$–$C_{20}$ straight or branched chain alkyl" includes alkyl radicals such as n-butyl, sec-butyl, tert-butyl, n-pentyl, n-hexyl, 2,2-dimethylbutyl, n-octyl, n-nonyl, 2,2-dimethylheptyl, n-decyl, n-hendecyl, 3-ethyl-2,3-dimethylhexyl, n-dodecyl, n-tridecyl, n-tetradecyl, n-pentadecyl, n-hexadecyl, n-heptadecyl, n-octadecyl, n-nonadecyl, n-eicosyl and the like.

The term "$C_4$–$C_{20}$ cycloalkyl" refers to cycloalkyl radicals containing a total of from 4 to 20 carbon atoms, inclusive such as cyclobutyl, 1-methycyclopentyl, cyclohexyl, etc.

The term "$C_8$–$C_{20}$ arylalkyl" refers to an alkyl radical containing a total of 8 to 20 carbon atoms, and having an aryl group attached to a terminus of the alkyl side chain.

The term "aryl", as used herein, refers to phenyl, substituted phenyl, naphthyl, thienyl, pyridyl, and pyrrolyl, all of which can be unsubstituted or substituted by one or more halo, nitro, loweralkyl, amino, alkoxy, i.e. 4-fluorophenyl, 3-fluorophenyl, 2-methylphenyl, etc.

The term "pharmaceutically acceptable salts" refers to the non-toxic acid addition salts of suitable organic or inorganic acids such as the hydrochloride, hydrobromide, sulfate tartrate, citrate, acetate, valerate, laurate, borate, naphsylate, oleate, etc.

Compounds of formulae I, II and III are useful as antihypertensive agents.

Generally speaking the following reaction schemes summarize the preparation of the compounds of the present invention:

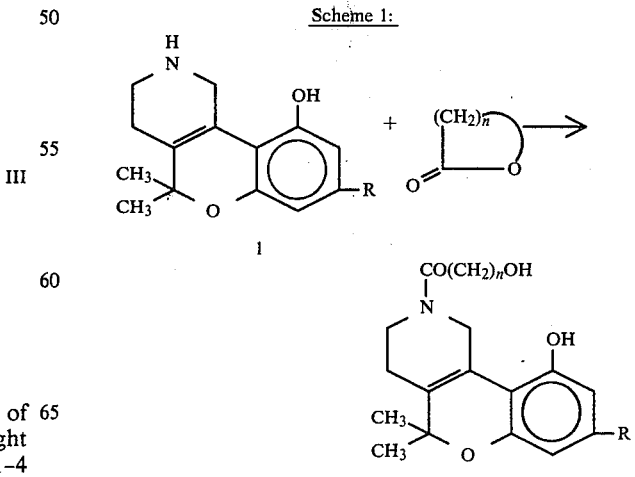

-continued

Scheme 2:

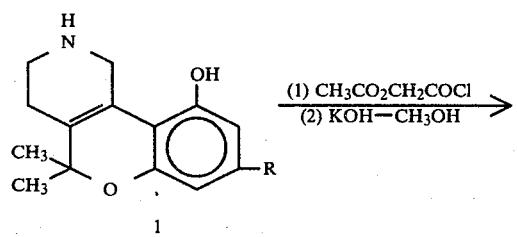

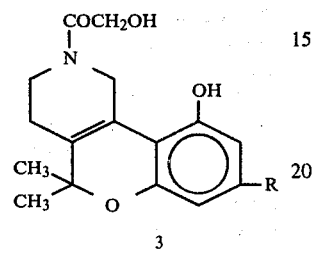

Scheme 3:

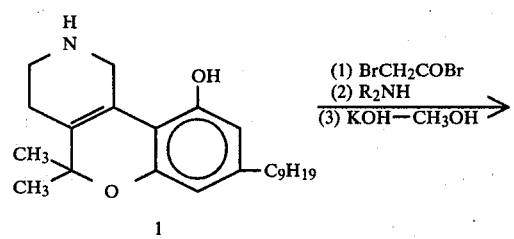

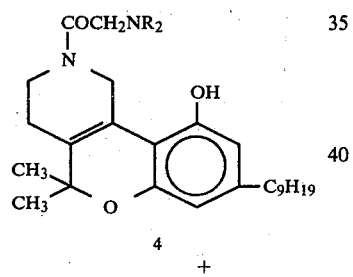

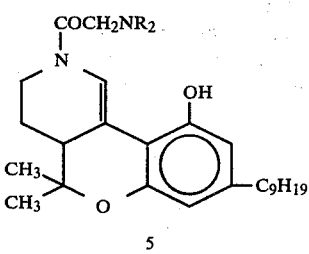

[$C_9H_{19}$ = —$CH(CH_3)CH(CH_3)$—n-$C_5H_{11}$]

Scheme 4:

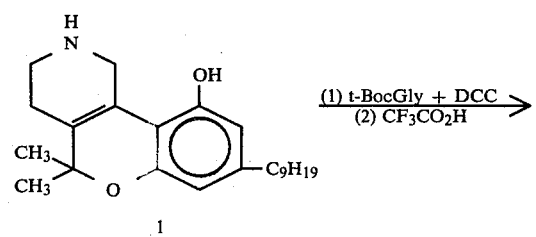

-continued

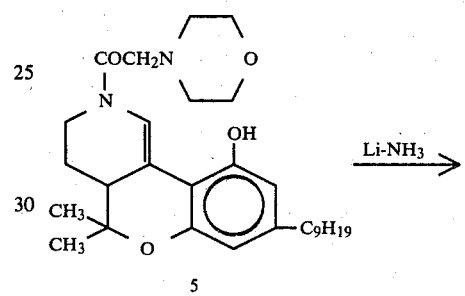

Scheme 5:

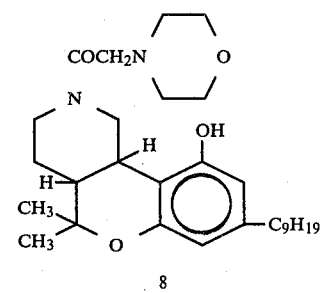

DETAILED DESCRIPTION OF PREFERRED EMBODIMENTS

The 2,8-disubstituted-10-hydroxy-5,5-dimethyltetrahydro-and hexahydro-5H-[1]-benzopyrano[4,3-c]pyridines of the present invention are useful as antihypertensive agents when administered to hypertensive patients in oral or parenteral doses of from about 3 to 30 mg daily, preferably from about 10 to 15 mg daily in divided dosages, e.g. 2 to 3 times daily For management of hypertension, the compounds are generally administered by the oral route of administration. However, the antihypertensive agents of the present invention are administered by parenteral routes of administration, i.e. intravenously, intramuscularly or peritoneally, during acute hypertensive crises, or in patients unable to take any medication per os.

The present invention includes within its scope pharmaceutical compositions comprising, as an active ingredient, at least one of the compounds of this invention in association with a pharmaceutically acceptable carrier or diluent. The compounds of this invention can be administered, as stated above, by oral or parenteral routes of administration, and can be formulated into dosage forms appropriate for each route of administration.

Solid dosage forms for oral administration include capsules, tablets, pills, powders and granules. In such solid dosage forms, the active compound is admixed with at least one inert diluent such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art such as water. Besides inert diluents, such compositions can also include adjuvanets such as wetting agents, emulsifying and suspending agents, and sweetening, flavoring and perfuming agents.

Preparations according to this invention for parenteral administration include sterile aqueous or nonaqueous solutions, suspensions or emulsions. Examples of non-aqueous solvents or vehicles are propylene glycol, polyethylene glycol, vegetable oils such as olive oil, and injectable organic esters such as ethyl oleate. Such dosage forms may also contain adjuvants such as preserving, wetting, emulsifying and dispersing agents. They may be sterilized by, for example, filtration through a bacteriaretaining filter, by incorporating sterilizing agents into the compositions, by irradiating the compositions, or by heating the compositions. They also can be manufactured in the form of sterile solid compositions which can be dissolved in sterile water, or some other sterile injectable medium immediately before use.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, whether or not the drug is taken alone or combined with diuretic therapy, and on the duration of treatment and dose response of the individual patient.

The following examples further illustrate the present invention.

EXAMPLE 1

Preparation of
5,5-dimethyl-8-[5-(4-fluorophenyl)-2-pentyl]-10-hydroxy-2-(4-hydroxybutyryl)-1,2,3,4-tetrahydro-5H-[1]benzopyrano[4,3-c]pyridine Formula I

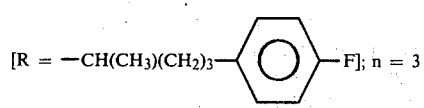

[R = —CH(CH$_3$)(CH$_2$)$_3$—⟨O⟩—F]; n = 3

A stirred solution of 0.01 mole of Compound 1, Reaction Scheme 1,

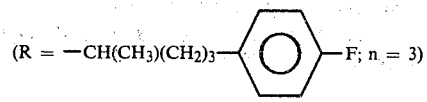

(R = —CH(CH$_3$)(CH$_2$)$_3$—⟨O⟩—F; n = 3)

[M. Winn, et al., J. Med. Chem., 19,461 (1976)] in 20 ml of dimethylformamide was treated with 1.73 g(0.02 mole) of γ-butyrolactone and heated in an oil bath at 100° C. for 4.5 hours. The mixture was concentrated to a small volume by distillation, taken up in a mixture of water and ether, washed successively with 1 N hydrochloric acid and water, and dried over anhydrous magnesium sulfate. Filtration and removal of the ether by distillation gave 4.14 g of a tan-colored, friable glass. This material was chromatographed on silica gel 60 using 2 percent methanol in ethyl acetate as the elution solvent. There was obtained 1.10 g of the title compound as a light tan amorphous glass: R$_f$(15 percent ethanol in toluene)=0.36;, mass spectral analysis, calculated for C$_{29}$H$_{36}$FNO$_4$: m/e, 481.2628. Found; m/e, 481.2620.

EXAMPLE 2

Preparation of
5,5-dimethyl-8-(1,2-dimethylheptyl)-10-hydroxy-2-(4-hydroxybutyryl)-1,2,3,4-tetrahydro-5H-[1]benzopyrano[4,3-c]pyridine(Formula I,[R=CH(CH$_3$)CH(CH$_3$)-n-C$_5$H$_{11}$], n=3

The above titled compound was prepared by reacting Compound 1 of Scheme 1 wherein R=CH(CH$_3$)CH(CH$_3$)-n-C$_5$H$_{11}$ (Pars, et al., J. Med. Chem., 19,445 (1976) with gamma-butyrolactone according to the method Example 1. The product was purified by chromatography on a column of 100–200 mesh Florisil (diatomaceous earth), using ethyl acetate for elution, and recrystallized from acetonitrile, m.p. 126–129° C. R$_f$(10 percent methanol in chloroform)=0.45.

Analysis Calcd. for C$_{27}$H$_{41}$NO$_4$:C,73.09; H, 9.31; N, 3.15. Found: C, 72.74; H, 9.84; N, 2.93.

EXAMPLE 3

Preparation of
5,5-dimethyl-8-(1,2-dimethylheptyl)-10-hydroxy-2-(3-hydroxypropionyl)-1,2,3,4-tetrahydro-5H-[1]benzopyrano[4,3-c]pyridine [Formula I, R=—CH(CH$_3$)CH(CH$_3$)-n-C$_5$H$_{11}$; n=2]

A stirred suspension of 20 g(0.056 mole) of Compound 1, Reaction Scheme 1, [R=—CH(CH$_3$)CH(CH$_3$)-n-C$_5$H$_{11}$]in 60 ml of dry ether was treated dropwise under an atmosphere of nitrogen, with a solution of 4.4 g of beta-propiolactone in 20 ml of dry ether. The reaction temperature was maintained at 23–25° C. with a cold water bath. After being stirred at room temperature for 48 hours, precipitated carboxylic acid by-product (18.4 g) was removed by filtration, and washed with dry ether. The filtrate and washings were combined and were washed successively with 2 N potassium bicarbonate and water, and dried over anhydrous magnesium sulfate. Filtration and concentration to dryness gave 2.8 g of crude product as a strawcolored friable glass. It was purified by chromatography on a column of silica gel 60 using ethyl acetate as the elution solvent. There as obtained 1.86 g of the above-titled compound as a colorless glass which could be recrystallized from hexane, m.p. 84–87° C.; $R_f$(10 percent methanol in chloroform) =0.50

Analysis Calcd. for $C_{26}H_{39}NO_4$:C, 72.69, H, 9.15; N, 3.26. Found: C, 72.30; H, 9.45; N, 3.17.

EXAMPLE 4

Preparation of 5,5-dimethyl-8-[5-(4-fluorophenyl)-2-pentyl]-10-hydroxy-2-hydroxyacetyl-1,2,3,4-tetrahydro-5H-[1]benzopyrano [4,3-c]pyridine, Scheme 2, Compound 3

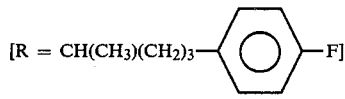

An ice-cold stirred suspension of 8.64 g (0.02 mole) of the hydrochloride salt of Compound 1

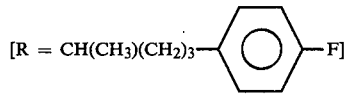

in 60 ml of methylene chloride was treated dropwise with 6.56 g (0.048 mole) of acetoxyacetyl chloride at such a rate as to keep the temperature below 5° C. This was followed by addition of 6.8 g (0.068 mole) of triethylamine keeping the temperature below 6° C. The mixture was stirred in an ice bath under an atmosphere of nitrogen for 4 hours and then at room temperature overnight. Ice and water were added to the mixture which was stirred until it once again returned to room temperature. The organic layer was separated, washed successively with 5 percent aqueous sodium bicarbonate and water, and concentrated to dryness. The residual thick, brown oil (13.12 g) was dissolved in 100 ml of methanol and, under a nitrogen atmosphere was treated with 10 ml of 45 percent aqueous potassium hydroxide. After being stirred at room temperature for one hour, the mixture was treated with 6 N hydrochloric acid to a pH of 2–3, and then was concentrated to dryness. The residue was taken up in a mixture of water and methylene chloride, separated, washed with water to neutrality and dried over anhydrous magnesium sulfate. Filtration and removal of the solvent by distillation gave 9.1 g of cream-colored crystalline powder that was recrystallized from acetonitrile (25 ml) to give 7.97 g of pure product, m.p. 146°–148° C.

Analysis Calcd. for $C_{27}H_{32}FNO_4$:C, 71.49; H, 7.11; N, 3.08. Found: C, 71.62; H, 7.40; N, 3.12.

EXAMPLE 5

Preparation of 5,5-Dimethyl-8-(1,2-dimethylheptyl)-10-hydroxy-2-hydroxyacetyl-1,2,3,4-tetrahydro-5H-[1]benzopyrano[4,3-c]pyridine, Scheme 2, Compound 3
[R=—CH(CH_3)CH(CH_3)—n—C_5H_{11}]

The above titled compound was prepared by treating compound 1[R=—CH(CH_3)CH(CH_3)-n-C_5H_{11}] with acetoxyacetyl chloride according to the method of Example 4, followed by saponification of the intermediate ester as described above. The latter was purified by recrystallization from acetonitrile, m.p. 125°–127° C.

Analysis Calcd. for $C_{25}H_{37}NO_4$:C, 72.25; H, 8.97; N, 3.37. Found: C, 71.95; H, 9.09; N, 3.29.

EXAMPLE 6

Preparation of 5,5-dimethyl-8-(1,2-dimethylheptyl)-10-hydroxy-2-morpholinoacetyl-2,3,4,4a-tetrahydro-5H-[1]-benzopyrano[4,3-c]pyridine, Scheme 3, compound 5

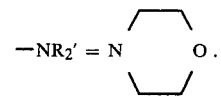

To an ice cold, stirred solution of 7.16 g (0.02 mole) of compound 1 (Scheme 3) in 40 ml of methylene chloride were added dropwise 9.70 g (0.048 mole) of bromoacetyl bromide dissolved in 10 ml of methylene chloride followed by a solution of 4.84 g (0.048 mole) of triethylamine in 10 ml of methylene chloride. The temperature was maintained below 8° C. during both additions. The reaction mixture was stirred in an ice bath for 1.5 hours and then at room temperature for 4 hours. Most of the solvent was removed under a rapid stream of nitrogen in a water bath held at 35°–40° C. The residue was taken up in 40 ml of dry dimethylformamide cooled in ice and treated dropwise with 8.71 g (0.10 mole) of morpholine, keeping the reaction temperature below 15° C. After being stirred at room temperature overnight, the reaction mixture was poured into water, insoluble material was taken up in methylene chloride, washed with water and concentrated to dryness. The residue (11.3 g) was taken up in 100 ml of methanol, cooled in ice, treated with 10 ml of 45 percent potassium hydroxide solution and stirred at room temperature under a nitrogen atmosphere for 2 hours. The solution was cooled in ice and neutralized to pH 9 (approximate) using 6 N hydrochloric acid and dry ice. The precipitate (about 11 g) was collected at the filter and shaken with a mixture of water and methylene chloride until solution was complete. The organic layer was separated, washed with water and concentrated to dryness. The crystalline residue (5.0 g), m.p. 205°–215° C., was recrystallized from dimethoxyethane to give 2.76 g of the above-titled compound, m.p. 217°–219° C.

Analysis Calcd. for $C_{29}H_{44}N_2O_4$:C, 71.86; H, 9.15; N, 5.78. Found: C, 71.86; H, 9.26; N, 5.92.

EXAMPLE 7

Preparation of 5,5-dimethyl-8-(1,2-dimethylheptyl)-10-hydroxy-2-morpholinoacetyl-1,2,3,4-tetrahydro-5H-[1]benzopyrano[4,3-c]pyridine

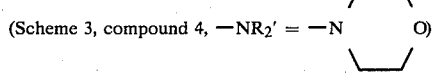

All soluble fractions and recrystallization residues obtained from the work-up procedure of Example 6 were combined and, after removal of all solvents by distillation, were chromatographed (5.45 g) on a column of silica gel 60 using ethyl acetate as the elution solvent. Material of higher $R_f$ proved to be more (1.01 g) of the product of Example 6, while the main fraction of lower $R_f$ was the above titled compound (2.29 g).

The latter was purified by recrystallization from hexane, m.p. 104°–106° C.

Analysis Calcd. for $C_{29}H_{44}N_2O_4$:C, 71.86; H, 9.15; N, 5.78. Found: C, 17.97; H, 9.50; N, 5.78.

EXAMPLE 8

Preparation of 5,5-dimethyl-8-(1,2-dimethylheptyl)-10-hydroxy-2-piperidinoacetyl-2,3,4,4a-tetrahydro-5H-[1]benzopyrano[4,3-c]pyridine, Scheme 3, compound 5,

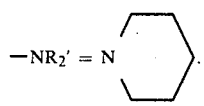

The above titled compound was prepared according to the method of Example 6 by substituting piperidine for morpholine in the second step. The product was purified by recrystallization from dimethoxyethane, m.p. 220°–222° C.

Analysis Calcd. for $C_{30}H_{46}N_2O_3$: C, 74.64; H, 9.60; N, 5.80. Found: C, 74.65; H, 9.90; N, 5.61.

EXAMPLES 9 AND 10

Preparation of 5,5-dimethyl-8-(1,2-dimethylheptyl)-2-glycyl-10-hydroxy-2,3,4,4a-tetrahydro-5H-[1]benzopyrano[4,3-c]pyridine(Scheme 4, Compound 7) and 5,5-dimethyl-8-(1,2-dimethylheptyl)-2-glycyl-10-hydroxy-1,2,3,4-tetrahydro-5H-[1]benzopyrano[4,3-c]pyridine (Scheme 4, compound 6)

A stirred solution of 8.94 g (0.025 mole) of compound 1 (Scheme 4) and 4.82 g (0.0275 mole) of t-butoxycarbonylglycine in 40 ml of dry dioxan was treated with 5.68 g (0.0275 mole) of solid dicyclohexylcarbodiimide. The reaction temperature rose to 38° C. and then decreased. After being stirred at room temperature for 22 hours, the reaction mixture was filtered from dicyclohexylurea (5.51 g, 89%) and concentrated nearly to dryness in a rotary evaporator. The residue was dissolved in ether, washed successively with water, 5% sodium bicarbonate solution and water, and dried over anhydrous magnesium sulfate. Filtration and concentration to dryness gave a straw-colored, amorphous glass (12.88 g) that could not be induced to crystallize. A 10.8 g sample of the material dissolved in methylene chloride was cooled in ice and treated with 30 ml of trifluoroacetic acid in one portion. After being stirred at room temperature for 1.5 hours, it was poured onto ice, extracted with ether, washed successively with water, 5% sodium bicarbonate solution and water, and dried over anhydrous sodium sulfate. Filtration and concentration to dryness gave 8.91 g of a brown amorphous glass consisting of two major components as indicated by thin layer chromatography. The latter were separated by chromotagraphy on a 3.5×90 cm column packed with 230 g of Silica Woelm (36–63 μm particle size) and using for elution a solvent containing the volume ratio of 920 ethyl acetate:80 ethanol:10 concentrated ammonium hydroxide. The first of the two componenets to come through proved to be compound 7(4.16 g) which could be further purified by successive recrystallizations from ethyl acetate and dimethoxyethane, m.p. 18°–183° C., $R_f$=0.42(90 $CHCl_3$:10$CH_3OH$:2 concd.$NH_4OH$).

Analysis Calcd. for $C_{25}H_{38}N_2O_3$: C, 72.42; H, 9.23; N, 6.75. Found: C, 72.51; H, 9.64; N, 6.56.

The second component proved to be compound 6 and was obtained as a pale yellow amorphous powder (2.28 g), $R_f$=0.32 (90$CHCl_3$:10$CH_3OH$:2 concd. $NH_4OH$).

Analysis Calcd. for $C_{25}H_{38}N_2O_3$: C, 72.42; H, 9.23; N, 6.75. Found: C, 72.38;H, 9.64; N, 7.12.

EXAMPLE 11

Preparation of 5,5-Dimethyl-8-(1,2-dimethylheptyl)-10-hydroxy-2-morpholinoacetyl-trans-1,2,3,4,4a,10b-hexahydro-5H-[1]benzopyrano[4,3-c]pyridine (Scheme 5, Compound 8)

The above titled compound is prepared by reduction of compound 5(Scheme 5) with lithium in liquid ammonia using the procedure of R. A. Archer, et al. *J. Org. Chem.* 42, 2277 (1977).

I claim:

1. A 2,8-disubstituted benzopyranopyridine represented by the formulae:

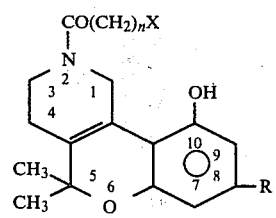

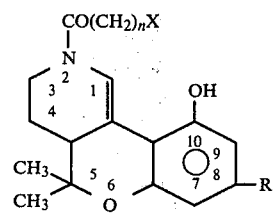

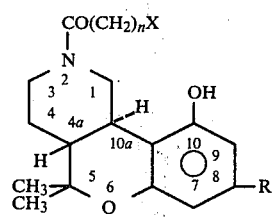

wherein: R is selected from the group consisting of $C_4$–$C_{20}$ straight or branched chain alkyl, $C_8$–$C_{20}$ straight or branched chain arylalkyl; n is an integer from 1–4 inclusive; and X is OH, $NR_1R_2$, $R_1$ and $R_2$ being the same or different members of the group consisting of hydrogen and loweralkyl, and

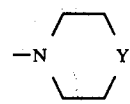

wherein Y is $CH_2$, S, O or $NR_1$; and the pharmaceutically acceptable salts thereof.

2. A benzopyranopyridine of claim 1 represented by the formula:

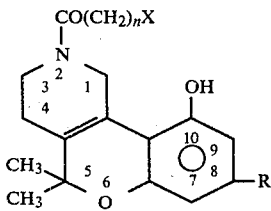

wherein R and X are as defined in claim 1, and the pharmaceutically acceptable salts thereof.

3. A benzopyranopyridine of claim 1 represented by the formula

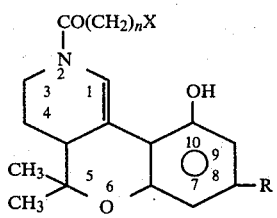

wherein R and X are as defined in claim 1, and the pharmaceutically acceptable salts thereof.

4. A benzopyranopyridine of claim 1 represented by the formula

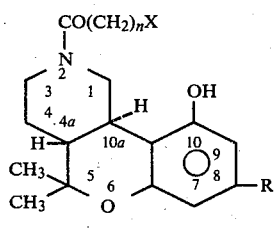

wherein R and X are as defined in claim 1, and the pharmaceutically acceptable salts thereof.

5. A benzopyranopyridine of claim 1, 2, 3 or 4 wherein R is $C_4$-$C_{20}$ straight or branched chain alkyl.

6. A benzopyranopyridine of claim 1, 2, 3 or 4 wherein R is arylalkyl.

7. A benzopyranopyridine of claim 1, 2, 3 or 4 wherein R is 1,2-dimethylheptyl.

8. A benzopyranopyridine of claim 1, 2, 3, or 4 wherein R is 5-(4-fluorophenyl)-2-pentyl.

9. A compound of claim 1: 5,5-dimethyl-8-[5-(4-fluorophenyl)-2-pentyl]-10-hydroxy-2-(4-hydroxybutyryl)-1,2,3,4-tetrahydro-5H-[1]benzopyrano[4,3-c]pyridine or a pharmaceutically acceptable salt thereof.

10. A compound of claim 1: 5,5-dimethyl-8-(1,2-dimethylheptyl)-10-hydroxy-2-(4-hydroxybutyryl)-1,2,3,4-tetrahydro-5H-[1]benzopyrano[4,3-c]pyridine or a pharmaceutically acceptacle salt thereof.

11. A compound of claim 1: 5,5-dimethyl-8-(1,2-dimethylheptyl)-10-hydroxy-2-(3-hydroxypropionyl)-1,2,3,4-tetrahydro-5H-[1]benzopyrano[4,3-c]pyridine or a pharmaceutically acceptable salt thereof.

12. A compound of claim 1: 5,5-dimethyl-8-[5-(4-fluorophenyl)-2-pentyl]-10 hydroxy-2-hydroxyacetyl-1,2,3,4-tetrahydro-5H-[1]benzopyrano[4,3-c]pyridine or a pharmaceutically acceptable salt thereof.

13. A compound of claim 1: 5,5-dimethyl-8-(1,2-dimethyheptyl)-10-hydroxy-2-hydroxyacetyl-1,2,3,4-tetrahydro-5H-[1]benzopyrano[4,3-c]pyridine or a pharmaceutically acceptable salt thereof.

14. A compound of claim 1: 5,5-dimethyl-8-(1,2-dimethylheptyl)-10-hydroxy-2-morpholinoacetyl-2,3,4,4a-tetrahydro-5H-[1]benzopyrano[4,3-c]pyridine or a pharmaceutically acceptable salt thereof.

15. A compound of claim 1: 5,5-dimethyl-8-(1,2-dimethylheptyl)-10-hydroxy-2-morpholinoacetyl-1,2,3,4-tetrahydro-5H-[1]benzopyrano[4,3-c]pyridine or a pharmaceutically acceptable salt thereof.

16. A compound of claim 1: 5,5-dimethyl-8-(1,2-dimethylheptyl)-10-hydroxy-2-piperidinoacetyl-2,3,4,4a-tetrahydro-5H-[1]benzopyrano[4,3-c]pyridine or a pharmaceutically acceptable salt thereof.

17. A compound of claim 1: 5,5-dimethyl-8-(1,2-dimethylheptyl)-2-glycyl-10-hydroxy-2,3,4,4a-tetrahydro-5H-[1]benzopyrano[4,3-c]pyridine or a pharmaceutically acceptable salt thereof.

18. A compound of claim 1: 5,5-dimethyl-8-(1,2-dimethylheptyl)-2-glycyl-10-hydroxy-1,2,3,4-tetrahydro-5H-[1]benzopyrano[4,3-c]pyridine or a pharmaceutically acceptable salt thereof.

19. A compound of claim 1: 5,5-dimethyl-8-(1,2-dimethylheptyl)-10-hydroxy-2-morpholinoacetyl-trans-1,2,3,4,4a,10b-hexahydro-5H-[1]benzopyrano[4,3-c]pyridine or a pharmaceutically acceptable salt thereof.

20. An antihypertensive composition comprising a therapeutically effective amount of a compound of claim 1 and a pharmaceutically acceptable carrier or diluent.

21. An antihypertensive composition comprising a therapeutically effective amount of the compound of claim 9 and a pharmaceutically acceptable carrier or diluent.

22. An antihypertensive composition comprising a therapeutically effective amount of the compound of claim 10 and a pharmaceutically acceptable carrier or diluent.

23. An antihypertensive composition comprising a therapeutically effective amount of the compound of claim 11 and a pharmaceutically acceptable carrier or diluent.

24. An antihypertensive composition comprising a therapeutically effective amount of the compound of claim 12 and a pharmaceutically acceptable carrier or diluent.

25. An antihypertensive composition comprising a therapeutically effective amount of the compound of claim 13 and a pharmaceutically acceptable carrier or diluent.

26. An antihypertensive composition comprising a therapeutically effective amount of the compound of claim 14 and a pharmaceutically acceptable carrier or diluent.

27. An antihypertensive composition comprising a therapeutically effective amount of the compound of claim 15 and a pharmaceutically acceptable carrier or diluent.

28. An antihypertensive composition comprising a therapeutically effective amount of the compound of claim 16 and a pharmaceutically acceptable carrier or diluent.

29. An antihypertensive composition comprising a therapeutically effective amount of the compound of claim 17 and a pharamceutically acceptable carrier or diluent.

30. An antihypertensive composition comprising a therapeutically effective amount of the compound of claim 19 and a pharmaceutically acceptable carrier or diluent.

31. A method of treating hypertension comprising administering a therapeutically effective amount of a compound of claim 1 to a hypertensive patient.

32. The method of claim 31 wherein said compound is administered orally to said hypertensive patient.

33. The method of claim 1 wherein said compound is administered parenterally to said hypertensive patient.

34. The method of claim 31 wherein said compound is administered in dosages of from 3 to 30 mg daily to said hypertensive patient.

* * * * *